United States Patent [19]

Caruso et al.

[11] Patent Number: 5,475,156
[45] Date of Patent: Dec. 12, 1995

[54] METHOD FOR MAKING A 2,6-DIALKYLPHENOL

[75] Inventors: Andrew J. Caruso, Schenectady; Julia L. Lee, Niskayuna, both of N.Y.

[73] Assignee: General Electric Company, Schenectady, N.Y.

[21] Appl. No.: 254,837

[22] Filed: Jun. 6, 1994

[51] Int. Cl.$^6$ .................. C07C 39/06; C07C 45/00
[52] U.S. Cl. .............. 568/780; 568/425; 568/426; 568/431; 568/432; 568/782
[58] Field of Search ................. 568/431, 426, 568/425, 780, 782, 784, 790, 432

[56] References Cited

U.S. PATENT DOCUMENTS

| | | | |
|---|---|---|---|
| 3,465,048 | 9/1969 | Ito et al. | 568/780 |
| 3,670,033 | 6/1972 | Izawa et al. | 568/780 |
| 3,875,247 | 4/1975 | Bourdin et al. | 568/780 |
| 4,533,767 | 8/1985 | Talley . | |
| 4,533,768 | 8/1985 | Talley . | |
| 4,560,810 | 12/1985 | Talley et al. . | |
| 4,870,215 | 9/1989 | Wiker et al. | 568/780 |
| 4,929,766 | 5/1990 | Schnatterer et al. . | |
| 5,091,594 | 2/1992 | Kupper et al. | 568/780 |

FOREIGN PATENT DOCUMENTS 240642  10/1987  Japan .

OTHER PUBLICATIONS

Article—The Oxidation of 2,4,6–Trimethylphenol with Molecular Oxygen Catalyzed by a Copper (II)–Oxime or Copper (II)–Amine System, M. Shimizu et al. The Chemical Society of Japan–Bull. Chem. Soc. Jpn., 66 (1993) 251–257.
Article—Novel Oxidation of Phenols by a Copper (II) Complex Catalyst/O2 System, K. Takehira et al. Elsevier Science Publishers B.V., Amsterdam (1991) 279–284.
Article—A Novel Oxygenation of 2,4,6–Trimethylphenol to 3,5–Dimethyl–4–Hydroxybenzaldehyde by Dioxygen with Copper (II)–Amine Complex Catalyst, K. Takehira et al. Tetrahedrom Letters, vol. 31, No. 18 (1990) 2607–2608.
Substituted–5,6,7,8–tetrahydroonaphthalene Derivatives, MS Newman & HV Zahn—Contribution from the Chemical Laboratory of the Ohio State University (Jun. 1943) pp. 1097–1101.
Article–K. Fries, E. Brandes, E. Annalen–Zur Kenntnis der Chinhonmethide (1939) pp. 48–77 (Article is in German but also attached is notation referred to as Ref.3a on separate sheet).

*Primary Examiner*—Werren B. Lone
*Attorney, Agent, or Firm*—William H. Pittman

[57] ABSTRACT

A method is provided for converting a 2,4,6-trialkylphenol, such as mesitol, to a dialkylphenol, for example 2,6-dimethylphenol, by effecting the selective oxidation of the 2,4,6-trialkylphenol, followed by the deformylation of the resulting 3, 5-dialkyl-4-hydroxybenzaldehyde.

12 Claims, No Drawings

METHOD FOR MAKING A 2,6-DIALKYLPHENOL

BACKGROUND OF THE INVENTION

The present invention relates to a method for converting a trialkylphenol, such as 2,4,6-trimethylphenol, or mesitol, to a dialkylphenol, such as 2,6-dimethylphenol, or 2,6-xylenol. More particularly, the present invention relates to a method for selectively oxidizing mesitol to 3,5-dimethyl-4-hydroxybenzaldehyde and thereafter effecting a deformylation of the benzaldehyde to produce 2,6-xylenol.

As shown by Talley, U.S. Pat. Nos. 4,533,767, 4,533,768, and 4,560,810, selective dealkylation of alkylated phenols can be achieved with steam in combination with various metal oxide catalysts, such as zinc oxide and optionally manganese oxide. Daly, U.S. Pat. No. 4,230,895 describes catalytic hydrodealkylation using mixtures of palladium and chromium oxide. Schnatterer U.S. Pat. No. 4,929,766 describes a process for converting p-cresol to p-hydroxy benzaldehyde employing oxygen in the presence of a solvent and a chelate complex of iron and/or manganese.

Although various techniques are available for dealkylating polyalkylated phenols, a satisfactory method for transforming a 2,4,6-trialkylphenol, such as mesitol, to 2,6-xylenol has not been developed. It would be a significant environmental advance if a method were developed to convert mesitol, which has limited utility and is often burned as a by-product to a useful end product, such as 2,6-xylenol, a key intermediate in the manufacture of polyphenylene oxide.

SUMMARY OF THE INVENTION

The present invention is based on the discovery that a 2,4,6-trialkylphenol, can be converted to a 2,6-dialkylphenol in a two step process involving the selective oxidation of the 4-alkyl radical on the 2,4,6-trialkylphenol, and the deformylation of the resulting 3,5-dialkyl-4-hydroxybenzaldehyde. Oxidation of the 4-alkyl radical of the 2,4,6-trialkylphenol to the hydroxybenzaldehyde can be achieved with the use of an effective amount of a copper catalyst; the deformylation of the hydroxybenzaldehyde results in the production of the desired 2,6-dialkylphenol in high yields.

STATEMENT OF THE INVENTION

There is provided by the present invention, a method for making a 2,6-dialkylphenol, which comprises, (A) effecting the selective oxidation of the 4-alkyl radical on a 2,4,6-trialkylphenol in an oxygen containing atmosphere in the presence of an organic solvent and an effective amount of a copper catalyst at a temperature of 25° C. to 100° C., (B) treating the resulting 3,5-dialkyl-4-hydroxybenzaldehyde reaction product of (A) to produce a mixture having less than 5 ppm of copper, and, (C) effecting the deformylation of the 3,5-dialkyl- 4-hydroxybenzaldehyde of (B) at a temperature of 190° C. to 350° C. in the presence of a Group VIIIA, transition metal catalyst to produce a 2,6-dialkylphenol.

Some of the 2,4,6-trialkylphenols which can be converted to 2,6-dialkylphenols in accordance with the practice of the invention are 2,4,6-trimethylphenol, 2,4-dimethyl-6-butylphenol, 2,4-dimethyl- 6-propylphenol, and 2,6-dibutyl-4-methylphenol.

Various techniques can be used to selectively oxidize the 4-alkyl group on a 2,4,6-trialkylphenol to produce a 3,5-dialkyl-4-hydroxybenzaldehyde. A preferred oxidation procedure is to employ an oxygen containing gas, for example, elemental oxygen, or air, in the presence of an organic solvent, a copper salt, and an amine cocatalyst. An effective amount of the copper catalyst is 1000 ppm to 5000 ppm of copper based on the weight of the oxidation mixture.

Oxidation of the 2,4,6-trialkylphenol can be effected in accordance with a "sparging" procedure, whereby oxygen or air is bubbled into a reaction mixture, or a preferred "static" procedure, whereby an oxygen containing gas is used as an overhead atmosphere.

In instances where the sparging procedure is used, oxidation of the 2,4,6-trialkylphenol to the 3,5-dialkyl-4-hydroxybenzaldehyde can be effected in the presence of a copper salt catalyst, such as cuprous chloride, with a mixture of an alcohol, and an organic amine cocatalyst for example diethyl amine, acetone oxime, hydroxylamine hydrochloride, imidazole, 2,9-dimethyl-1,10-phenanthroline, or 2-hexylimidazole which can serve as the cocatalyst. An amide containing organic compound, such as a dialkylformamide, also can serve as a cocatalyst in place of the organic amine. However, the dialkylformamide, such as dimethylformamide, is generally used in an excessive amount (>500 mol %) relative to the trialkylphenol and has a high boiling point, for example 153° C., which makes its recovery and reuse difficult.

Copper salts which can be used as catalysts are for example, Cu(I)Cl or Cu(II)Cl$_2$. The copper salt can be used at from 1 mol % to 5 mol % based on the moles of trialkylphenol used.

Group VIIIA transition metal catalysts include iron, cobalt, nickel, ruthenium, rhodium, palladium, osmium, iridium and platinum. Palladium and rhodium are preferred.

Among the amide containing organic compounds there are included N,N-dimethylformamide, N,N-diethylformamide, N,N-dipropylformamide, N,N-dimethylacetamide, N,N-diethylformamide, N,N-dimethylpropionamide, N-formylpiperidine, N-formylpyrrolidine, acetylpiperidine, acetylpyrrolidine, formanilide, N-methylacetanilide, acetylpyridine, N-methyl-N-formyltoluidine, N-methyl-N-acetyltoluidine, dimethylbenzamide, tetramethylurea, N,N-dimethyltolylurea, succinimide, glutarimide, and phthalimide. Among these, there are especially preferred amide containing compounds, such as N,N-dimethylformamide, N,N-diethylformamide, N,N-dimethylacetamide, and tetramethylurea.

Some of the alcohols which can be used as solvents are C$_{(1-6)}$ alkanols, methanol, ethanol and propanol.

A preferred procedure for effecting the oxidation of the 2,4,6-trialkylphenol using the sparging procedure is to use imidazole as a cocatalyst. A relatively small amount (1–5 mol %) of the imidazole cocatalyst has been found effective in a continuously sparged oxidation mixture, as compared to >500 mol % for dimethylformamide.

In instances where static oxidation of the 2,4,6-trialkylphenol is used, there can be employed a copper catalyst in combination with a cocatalyst such as acetone oxime, or a dialkylamine. However, when using acetone oxime, or a dialkylamine, such as diethylamine as a cocatalyst, a solvent having a relatively high boiling point, such as hexanol, is required for a satisfactory conversion of the 2,4,6-trialkylphenol to the 3,5-dialkyl-4-hydroxybenzaldehyde. It is preferred therefore to use imidazole, or a substituted derivative thereof, such as 2-methylimidazole or 2-hexylimidazole or derivatives of the imidazole-containing amino acid histidine as a cocatalyst, because a lower boiling solvent such as methanol can be used. Another cocatalyst such as neocuproine hydrate also has been found effective with methanol.

Oxidation of the trialkylphenol to the 3,5-dialkyl- 4-hydroxybenzaldehyde can be effected at a temperature in the range of 10° C. to 70° C. at atmospheric pressure. Although oxygen is the preferred oxidizing agent, air also has been found effective. However, air must be used at a higher volume % and the risk of environmental problems is potentially greater.

In order to obtain a satisfactory yield of the 2,6-dialkylphenol from the 3,5-dialkyl- 4-hydroxybenzaldehyde, it is preferred that the deformylation mixture have less than 5 ppm of copper. A suitable work-up procedure can be used to reduce total copper in the 3,5-dialkyl-4-hydroxybenzaldehyde mixture to minimize potentially adverse side reactions in the subsequent deformylation reaction. One procedure is to filter the oxidation mixture of insoluble copper salts, remove the solvent such as methanol under reduced pressure and partition the residue between an organic solvent, such as ethyl acetate or toluene and an aqueous solution of a copper complexing agent such as ethylenediamine tetraacetic acid trisodium salt. Recrystallization of the resulting 3,5-dialkyl-4-hydroxybenzaldehyde will provide analytically pure product.

Deformylation of the 3,5-dialkyl-4-hydroxybenzaldehyde can be effected at a a temperature in the range of 190° C. to 350° C. at atmospheric pressure. An effective amount of the Group VIIIA transition metal catalyst, such as a palladium catalyst is 10 ppm to 50,000 ppm of palladium, based on the weight of deformylation mixture. It is preferred to use palladium on carbon (0.01% to 20% of Pd/C). Deformylation is preferably effected in an inert atmosphere such as nitrogen. An inert organic solvent can be used to facilitate recovery of 2,6-dialkylphenol and the deformylation catalyst.

In order that those skilled in the art will be better able to practice the invention, the following examples are given by way of illustration and not by way of limitation. All parts are by weight unless otherwise indicated.

EXAMPLE 1

A reaction mixture consisting of 136.2 g (1.00 mol) of mesitol, 5.00 g (0.05 mol) of CuCl powder, 140 ml of dimethylformamide, and 700 ml of methanol was sparged with oxygen (flow rate=1.2–1.5 liter/min) and heated in an oil bath at 70°–75° C. for eight hours. The mixture was then allowed to stand for twelve hours at ambient temperature. It was filtered through a pad of celite and concentrated under reduced pressure. After removal of most of the methanol, the residue was poured into 1.5 liters of water containing 18 g of ethylenediaminetetraacetic acid trisodium salt hydrate (EDTA-Na$_3$.2H$_2$O) and ethyl acetate to effect copper removal. The organic phase was further treated with EDTA-Na$_3$.2H$_2$O solution followed by water to provide a concentrate having less than 4.5 ppm of Cu. Recrystallization of the crude product in toluene provided pure 3,5-dimethyl-4-hydroxybenzaldehyde (DMHB).

A mixture was heated to 265°–275° C. under a nitrogen atmosphere consisting of 45.00 g ( assay=84.6% 253.8 mmol) , of 3, 5-dimethyl-4-hydroxybenzaldehyde, 107 mg 10% Pd on carbon (10.7 mg, 0.1 mmol Pd) and 45.00 g of tetradecane. After 4 hours, a 25:1 mixture of 2,6-xylenol and DMHB was obtained based on the use of a Gas Chromatograph (GC). The mixture was distilled under nitrogen at atmospheric pressure. A single fraction was collected (bp 190°–250° C.) which upon cooling afforded a yellow crystalline solid and a golden supernatant layer (total weight 64 g). The liquid layer was shown by GC analysis to be a tetradecane rich mixture of 2,6-xylenol and tetradecane and was decanted back into the reaction vessel. The yellow solid (39.86 g) was melted and assayed by $^1$H-NMR and shown to be a 3.6:1 mixture of 2,6-xylenol and tetradecane. The mixture was set aside while the original pot residue from the distillation as well as the tetradecane rich supernatant liquid was charged again with DMHB (45.00 g, assay=84.6%, 253.8 mmol). The mixture was heated for 3.5 hours at 280°–285° C. and then 10 minutes at 300°–310° C. GC at this point indicated a 2:1 mixture of 2,6-xylenol and starting DMHB. The reaction mixture was heated an additional 2 hours at 254°–255° C. and then distilled as before to afford a single fraction (bp 180°–250° C.) which separated into a crystalline lower and oily upper phases. The supernatant liquid (39.17 g) was decanted off. There was obtained 24.97 g of a solid which was assayed by $^1$H-NMR and found to consist of a 5:1 mixture of 2,6xylenol and tetradecane. These two fractions and the original 3.6:1 mixture of 2,6-xylenol and tetradecane were combined and assayed to provide a 87.2% yield of 2,6-xylenol (54.03 g). Total catalyst turnover=(442.9 mmol product 2,6-xylenol)/(0.1 mmol Pd)= 4429.

EXAMPLE 2

A mixture of 13.622 g(100 mmol) of mesitol, 285 mg (1.26 mmol) of neocuproine hydrate, 503 mg (5.0 mmol) of CuCl and 120 mL of methanol was stirred at ambient temperature for 9 hours under an oxygen blanket. The reaction mixture was then diluted with ethyl acetate and filtered. The methanol was stripped off and the residue diluted with additional ethyl acetate. The solution was washed twice with a 1% solution of ethylenediaminetetraacetic acid trisodium salt (EDTA-Na$_3$.2H$_2$O), water and brine, dried over MgSO$_4$ and concentrated. There was obtained 13.92 g of an orange-gold solid which was shown by $^1$H NMR and GC to contain 11.88 g (79.2% yield) of 3,5-dimethyl- 4-hydroxybenzaldehyde (DMHB).

A similar procedure was followed except that imidazole was substituted for neocuproine. The following table compares the results obtained in the present invention with cocatalysts found in the literature shown as acetone oxime, and diethylamine ((Et)$_2$NH):

| | Oxidation of Mesitol Under Static O$_2$ Pressure | | | | | | |
|---|---|---|---|---|---|---|---|
| Yield DMHB | mmol Cu-CAT | Co-cat. & level Ψ | Solvent | Rxn Temp. | Rxn Time | % Convers | O$_2$ P |
| 94.8% | 10 mol % CuCl$_2$ | 20 mol % aceoxim | hexanol | 60° C. | 1.5 h | 100% | 1.10 atm |
| 82.5% | 5 mol % CuCl$_2$ | 10 mol % aceoxim | hexanol | 60° C. | 2 h | 100% | 1.10 atm |
| 77.7% | 10 | 10 | hexanol | 60° C. | 4 h | 97.6% | 1.10 atm |

-continued

Oxidation of Mesitol Under Static O₂ Pressure

| Yield DMHB | mmol Cu-CAT | Co-cat. & level Ψ | Solvent | Rxn Temp. | Rxn Time | % Convers | $O_2$ P |
|---|---|---|---|---|---|---|---|
| 8.1% | mol % $CuCl_2$ 5 mol % | mol % $(Et)_2NH$ 10 mol % | MeOH | 40° C. | 5 h | 43.6% | 1.10 atm |
| 91.7% | $CuCl_2$ 10 mol % | aceoxim 20 mol % | hexanol | 60° C. | 0.75 h | 97.5% | 1.10 atm |
| 79.2% | $CuCl_2$ 5 mol % | aceoxim 1.25 mol % | MeOH | RT | 9 h | 100% | 1.03 atm |
| 81.2% | CuCl 5 mol % | neocupr 2.5 mol % | MeOH | 65° C. | 4 h | 100% | 1.03 atm |
| 83% | CuCl 5 mol % | imidaz 2.5 mol % | MeOH | 65° C. | 2 h | 100% | 1.03 atm |
|  | CuCl |  neocupr |  |  |  |  |  |

Ψ aceoxim = acetone oxime
neocupr = neocuproine hydrate
imidaz = imidazole
$(Et)_2NH$ = diethylamine The above results show that in converting mesitol to DMHB by the static oxidation procedure, the employment of neocuproine hydrate and imidazole as cocatalysts, allows for the use of methanol, (BP 64° C.) as a solvent, in place of hexanol (BP 157° C.).

As shown in example 1, the DMHB prepared above by the static procedure, can be converted to 2,6-xylenol.

Although the above examples are directed to only a few of the many variables which can be used in the practice of the present invention, it should be understood that the present invention is directed to the use of a much broader variety of 2,4,6-trialkylphenols, catalysts, and conditions as set forth in the description preceding these examples.

What is claimed is:

1. A method for making a 2,6-dialkylphenol, which comprises,
    (A) effecting the selective oxidation of the 4-alkyl radical on a 2,4,6-trialkylphenol in an atmosphere comprising air or elemental oxygen in the presence of a $C_{1-6}$ alkanol as solvent and an effective amount of a copper salt as catalyst and an organic amine or amide as cocatalyst at a temperature of 25° C. to 100° C.,
    (B) treating the resulting 3,5-dialkyl-4-hydroxybenzaldehyde reaction product of (A) to produce a mixture having less than 5 ppm of copper, and,
    (C) effecting the deformylation of the 3,5-dialkyl-4-hydroxybenzaldehyde of (B) at a temperature of 190° C. to 350° C. in the presence of a Group VIIIA metal catalyst to produce a 2,6-dialkylphenol.

2. A method in accordance with claim 1, where the 2,4,6-trialkylphenol is mesitol.

3. A method in accordance with claim 1, where the 2,6-dialkylphenol is 2,6-xylenol.

4. A method in accordance with claim 1, where the oxygen containing atmosphere is maintained by sparging.

5. A method in accordance with claim 1, where the oxygen containing atmosphere is statically maintained.

6. A method in accordance with claim 1, where an amide is used as a cocatalyst.

7. A method in accordance with claim 6, where the amide is diethylformamide.

8. A method in accordance with claim 1, where neocuproine is used as a cocatalyst.

9. A method in accordance with claim 1, where imidazole is used as a cocatalyst.

10. A method in accordance with claim 1, where the Group VIIIA metal catalyst is palladium.

11. A method for making a 3,5 dialkyl-4-hydroxybenzaldehyde comprising effecting the selective oxidation of the 4-alkyl radical on a 2,4,6-trialkylphenol in an atmosphere comprising air or elemental oxygen in the presence of an organic solvent and a copper salt as catalyst and an amine selected from the group consisting of neocuproine hydrate, imidazole, and derivatives thereof as cocatalyst.

12. A method in accordance with claim 10, where the 2,4,6-trialkylphenol is mesitol.

* * * * *